US009295852B1

(12) United States Patent
Williamson

(10) Patent No.: US 9,295,852 B1
(45) Date of Patent: Mar. 29, 2016

(54) SYSTEM AND METHOD FOR CONFIRMING HEART ARRHYTHMIA

(75) Inventor: Richard Williamson, Saugus, CA (US)

(73) Assignee: PACESETTER, INC., Sylmar, CA (US)

( * ) Notice: Subject to any disclaimer, the term of this patent is extended or adjusted under 35 U.S.C. 154(b) by 1232 days.

(21) Appl. No.: 11/197,996

(22) Filed: Aug. 4, 2005

(51) Int. Cl.
*A61N 1/39* (2006.01)

(52) U.S. Cl.
CPC ........................................ *A61N 1/39* (2013.01)

(58) Field of Classification Search
USPC ........................................................ 607/1–5
See application file for complete search history.

(56) References Cited

U.S. PATENT DOCUMENTS

| | | | | |
|---|---|---|---|---|
| 5,312,441 A | * | 5/1994 | Mader et al. ........................ | 607/5 |
| 5,350,401 A | | 9/1994 | Levine .............................. | 607/4 |
| 5,601,609 A | * | 2/1997 | Duncan ............................. | 607/5 |
| 5,766,225 A | * | 6/1998 | Kramm ............................. | 607/4 |
| 6,862,476 B2 | | 3/2005 | Mouchawar et al. ........... | 607/27 |
| 7,381,185 B2 | * | 6/2008 | Zhirnov et al. ................ | 600/300 |
| 2003/0204215 A1 | | 10/2003 | Gunderson et al. ............. | 607/27 |
| 2004/0215092 A1 | * | 10/2004 | Fischell et al. ................. | 600/515 |

FOREIGN PATENT DOCUMENTS

| | | | | |
|---|---|---|---|---|
| WO | WO 03/092810 A2 | 11/2003 | ............... | A61N 1/39 |
| WO | WO 2004/015197 A1 | 2/2004 | ............... | D21F 7/00 |
| WO | WO 2004/023995 A1 | 3/2004 | ........... | A61B 5/0456 |
| WO | WO 2004/093974 A2 | 11/2004 | ............... | A61N 1/37 |
| WO | WO 2004/093974 A3 | 11/2004 | ............... | A61N 1/37 |

* cited by examiner

*Primary Examiner* — Rex R Holmes

(57) ABSTRACT

A system and method for confirming arrhythmias in an implantable cardiac stimulation device senses electrical events in an intracardiac signal and identifies a potential arrhythmia based on the electrical events. The electrical events may be depolarization events occurring in a heart, such as R-waves or P-waves. The electrical events are high pass filtered and analyzed to confirm or reject the electrical events. The confirmed electrical events are then analyzed to determine whether the electrical events indicate a heart arrhythmia. A therapy may then be applied to the heart for treating the arrhythmia.

8 Claims, 7 Drawing Sheets

SYSTEM AND METHOD FOR CONFIRMING HEART ARRHYTHMIA

BACKGROUND

Typical implantable cardiac stimulation devices such as pacemakers or implantable cardioverter defibrillators (ICDs) are capable of detecting arrhythmias and applying therapy to the heart. An arrhythmia is an abnormal heart beat pattern. One example of arrhythmia is bradycardia wherein the heart beats at an abnormally slow rate or wherein significant pauses occur between consecutive beats. Other examples of arrhythmias include tachyarrhythmias wherein the heart beats at an abnormally fast rate. In atrial tachycardia, the atria of the heart beat abnormally fast. In ventricular tachycardia, the ventricles of the heart beat abnormally fast. Though often unpleasant for the patient, a tachycardia is typically not fatal. However, some types of tachycardia, particularly ventricular tachycardia, can accelerate into ventricular fibrillation (VF). Ventricular fibrillation is an arrhythmia wherein the heart beats chaotically such that there is little or no net flow of blood from the heart to the brain and other organs. Ventricular fibrillation, if not terminated within minutes, is fatal. Hence, it is highly desirable to prevent or terminate arrhythmias, particularly arrhythmias of the type that can lead to ventricular fibrillation.

An arrhythmia is typically treated by delivering electrical shocks to the heart to restore a natural sinus rhythm in which the heart beats at a normal rate. Failure to promptly detect an arrhythmia (such as a low amplitude ventricular fibrillation) can result in a delay in the delivery of electrical shocks with a reduced likelihood of restoring the sinus rhythm. In this regard, it has been proposed to use the detection of loss of capture (LOC) of a series of ventricular pacing pulses as a means for detecting low amplitude VF and for triggering delivery of a high output defibrillation shock. See U.S. Pat. No. 5,350,401, by Levine, which is incorporated herein by reference. With that technique, upon detection of loss of capture of a ventricular pulse, the ventricular pulse output magnitude is increased and another pulse is delivered. If that pulse also fails to capture, the output magnitude is increased again. This process proceeds until either a ventricular pulse captures or until a maximum pulse output level is reached. If the maximum output is reached and the ventricular pulses still do not evoke capture, a determination is thereby made that a low amplitude VF may have occurred and a defibrillation shock may be delivered to terminate the VF. Although the technique is effective in eventually detecting low amplitude VF, the need to deliver a series of ventricular pulses with different pulse magnitudes delays the detection of VF, thus potentially reducing the effectiveness of subsequent shock therapy.

Thus, conventional arrhythmia detection techniques do not always detect arrhythmias as quickly as desired, resulting in a reduced likelihood that subsequent therapy will be successful. Conversely, conventional arrhythmia detection techniques may incorrectly detect arrhythmias, resulting in inappropriate therapy. In these situations, electrical shocks are delivered to the heart when no therapy is desired. Consequently, the patient may experience sensations such as pain from the electrical shocks when the patient's heart is functioning normally. In light of the above, there exists a need for improving the accuracy and reliability of heart arrhythmia detection.

SUMMARY

In accordance with certain implementations and embodiments, systems and methods are provided for use with implantable cardiac stimulation devices for accurately and reliably detecting the onset of heart arrhythmias. In various embodiments, an electrical event occurring in the ventricle of a heart is sensed and a check is performed to confirm that the electrical event is a depolarization event of the heart. The confirmation is typically done by ensuring that sufficient high frequency electrical activity is detected, as depolarization events are typically higher in frequency than repolarization events. The confirmed electrical event may be used to improve detection or confirmation of the onset of tachycardia or fibrillation in a patient's heart. A therapy of electrical shocking pulses may then be applied to the heart for treating the arrhythmia. By confirming that the detected electrical event is a depolarization event, the reliability of detecting arrhythmias may be improved, which may reduce inappropriate therapy applied to the patient's heart.

A method capable of use in an implantable cardiac stimulation device in accordance with one implementation includes identifying a potential arrhythmia, performing a confirmation that sensed events of the arrhythmia are depolarization events associated with the potential arrhythmia, and determining whether to deliver therapy based on the confirmation of the sensed events.

A method for use in an implantable cardiac stimulation device in accordance with one implementation includes sensing a first electrical event of a heart in a first signal, high pass filtering the first electrical event to generate a second signal, and confirming the first electrical event based on the second signal.

An implantable cardiac stimulation device in accordance with one embodiment of the present invention includes an arrhythmia detector and a confirmation unit. The arrhythmia detector is capable of identifying electrical events of a heart and identifying a potential arrhythmia in the heart based on the electrical events. The confirmation unit is capable of confirming the electrical events by high pass filtering the electrical events so that the implantable cardiac stimulation device is capable of determining whether to deliver therapy to the heart.

An implantable cardiac stimulation device in accordance with another embodiment of the present invention includes electrodes for sensing electrical events in a heart and for delivering therapy to the heart, and a processor having processor executable instructions for performing a method comprising identifying a potential arrhythmia based on the electrical events, confirming the electrical events, and determining whether to deliver therapy based on the confirmed electrical events.

A system in an implantable cardiac stimulation device in accordance with one embodiment of the present invention includes an arrhythmia detector and a confirmation unit. The arrhythmia detector is configured to sense a first electrical event of a heart in a first signal. The confirmation unit is configured to confirm the first electrical event.

BRIEF DESCRIPTION OF THE DRAWINGS

Further features and advantages of the invention may be more readily understood by reference to the following description taken in conjunction with the accompanying drawings.

DESCRIPTION

Figure 1:
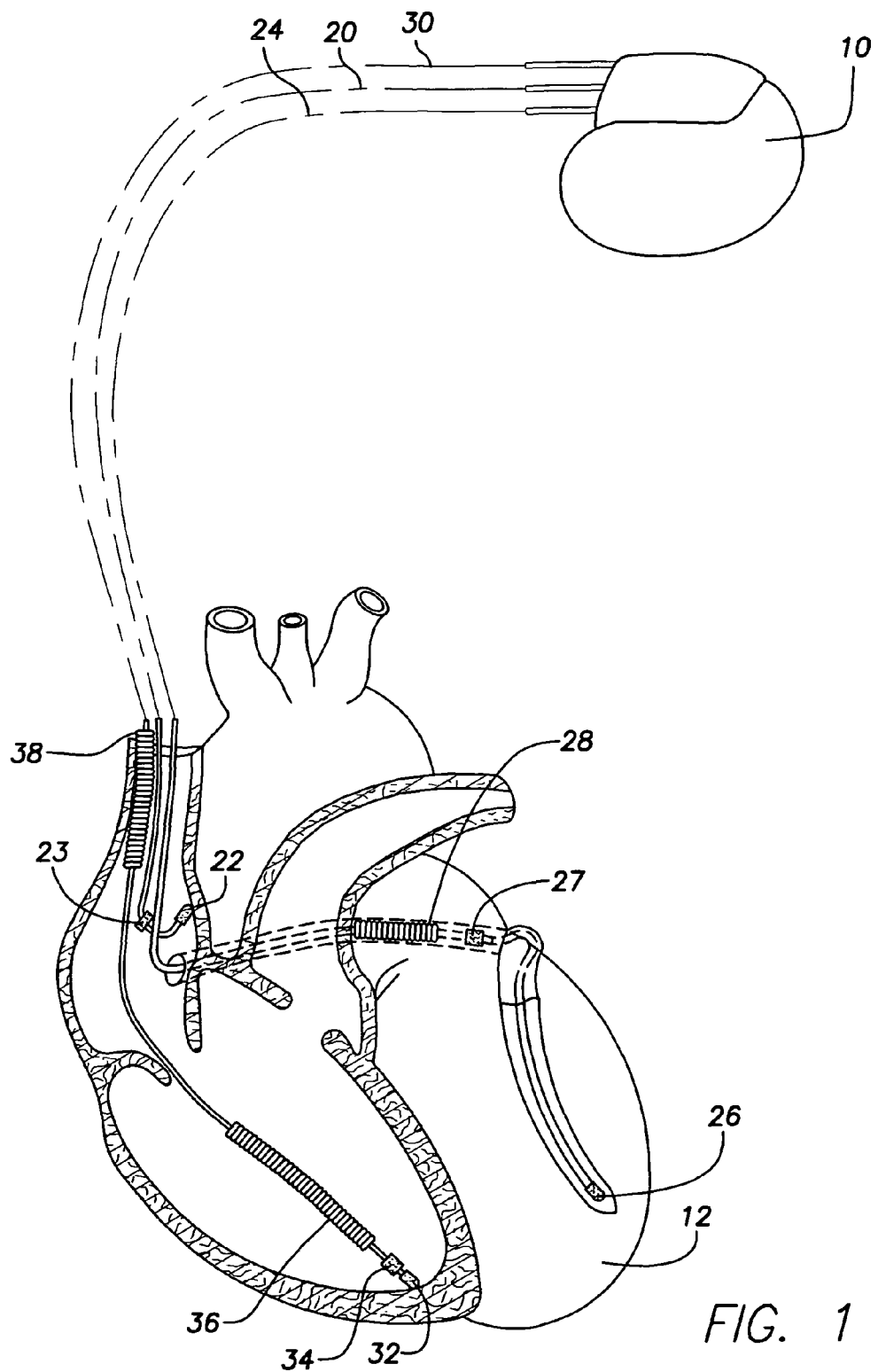
FIG. 1 is a simplified diagram illustrating a stimulation device in electrical communication with leads implanted into the heart of a patient for delivering shock therapy in accordance with one embodiment of the present invention.

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

An arrhythmia may be detected by analyzing an intracardiac signal, such as an electrogram signal, that represents electrical events occurring in a patient's heart. The electrical events may include a repolarization of the heart, which is often called a T-wave, and a depolarization event of the heart, which is often called an R-wave. The arrhythmia is detected by sensing R-waves in the intracardiac signal, and analyzing the pattern and or type of R-waves to identify the arrhythmia.

An R-wave may be sensed by determining when the absolute value of a voltage amplitude of the intracardiac signal exceeds a voltage threshold. This voltage threshold may be adjusted to a level just below a previously sensed R-wave and may be a declining threshold. Because an R-wave typically has a higher voltage peak than that of a T-wave, the R-wave may be distinguished from the T-wave based on the voltage threshold. In some cases, the voltage amplitude of an R-wave drops to the same level as that of a T-wave, which is sometimes referred to as "R-wave drop". Consequently, the T-wave may be incorrectly sensed as an R-wave, which may result in an incorrect identification of an arrhythmia. This incorrect sensing of a T-wave is often referred to as T-wave oversensing. One example of this type of sensing method is disclosed in U.S. Pat. No. 6,862,476, by Mouchawar, et al., entitled "Implantable Cardiac Stimulation Device Having Automatic Sensitivity Control and Method," issued Mar. 1, 2005, herein incorporated by reference in its entirety.

Various techniques may be used for reducing T-wave oversensing and thus improve the accuracy of arrhythmia identification. One technique for reducing T-wave oversensing is a timing stability method. In the timing stability method, R-waves are sensed in the electrogram signal, and one or more timing patterns are identified based on stable or regular intervals between the sensed R-waves. In the case of T-wave oversensing, a first timing pattern may be identified for R-waves and a second timing pattern may be identified for T-waves that may have been incorrectly sensed as R-waves. The R-waves of the second timing pattern are then discarded and the remaining R-waves are analyzed for the presence of an arrhythmia. However, the timing stability method may not detect a distinct timing pattern for T-waves if only a small number of heart beats are analyzed or if the T-waves are exactly between the R-waves. Consequently, T-wave oversensing may occur in the timing stability method. Moreover, the timing stability method may identify a timing pattern for a competitive heart rhythm caused by a premature ventricular contraction, which may occur at the start of tachycardia. In this situation, the timing pattern for the competitive heart rhythm is discarded and, thus, the tachycardia is not identified or treated.

Another technique for reducing T-wave oversensing is a morphology method. In the morphology method, a sensed R-wave is compared with templates of standard R-waves to determine whether the sensed R-wave matches any of the templates. For instance, the shape of the sensed R-wave may be correlated with the shapes of the templates. The morphology method may distinguish R-waves from T-waves for tachycardia detection but may not reliability detect R-waves for fibrillation detection because of the chaotic nature of an electrogram signal during fibrillation. Thus, T-wave oversensing may occur when using the morphology method for fibrillation detection.

Another technique proposed for reducing T-wave oversensing is the signal power method. In the signal power method, the power of a sensed R-wave is compared to a threshold power level, which may be a rolling average power level. However, if the amplitudes of R-waves drop to the amplitude of T-waves, the R-waves will have a power that is close to the power of the T-waves and thus the R-waves may not be reliably distinguished from the T-waves. Consequently, T-wave oversensing may occur in the signal power method.

In various embodiments of the present invention, R-waves are detected in an electrogram signal and confirmed based on the presence of high-frequency components in the detected R-waves. In other embodiments of the present invention, R-waves are detected in an electrogram signal and confirmed by using the timing stability method, the morphology method, or the signal power method. The confirmed R-waves are then confirmed (i.e., reconfirmed) based on the presence of high-frequency components in the R-waves.

Implantable Stimulation Device

FIG. 1 illustrates a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage, and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, in some embodiments, an exemplary coronary sinus lead 24 is designed to receive atrial and ventricular cardiac signals and to deliver left ventricular pacing therapy using at least a left ventricular tip electrode 26, left atrial pacing therapy using at least a left atrial tip electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
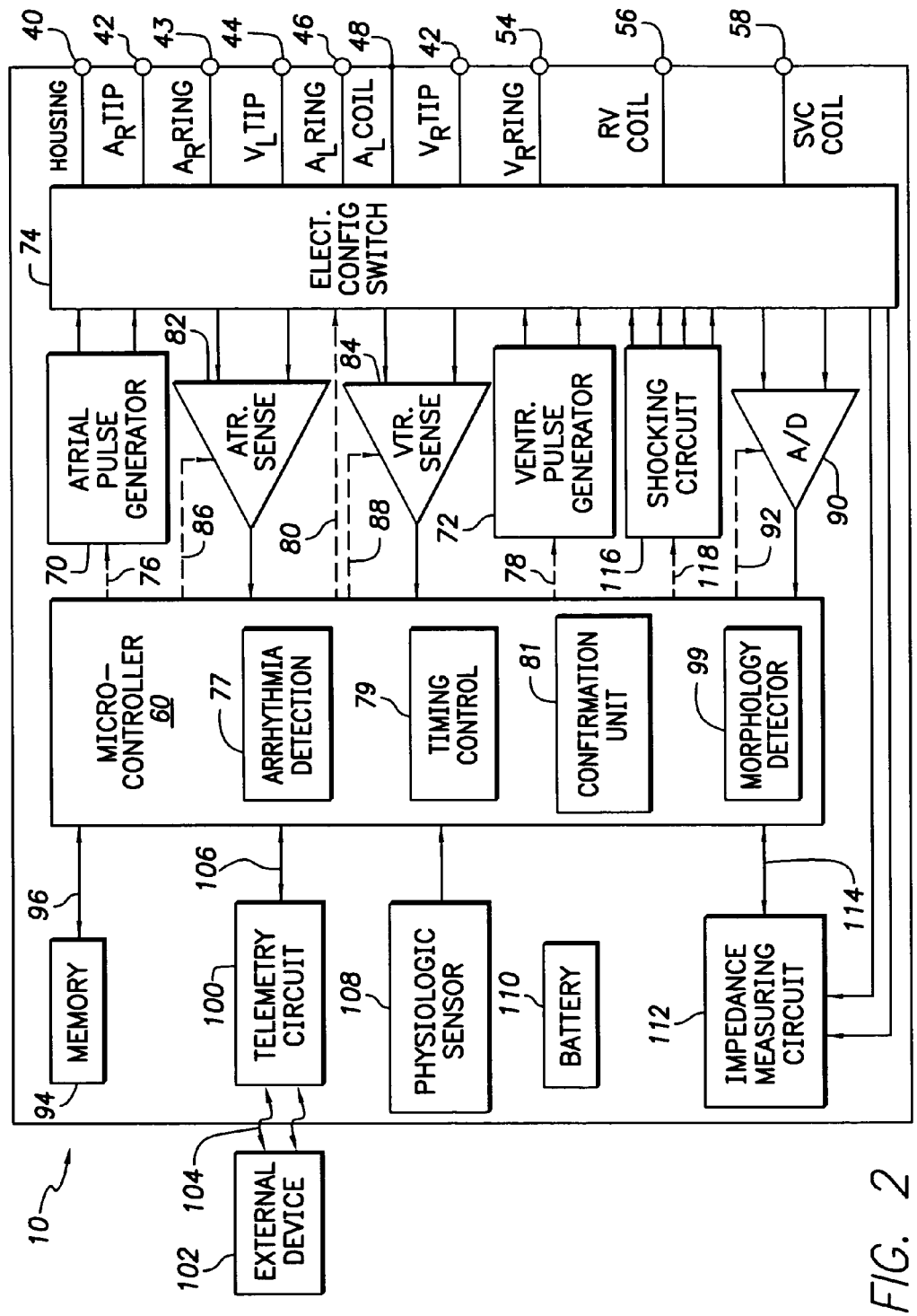
FIG. 2 is a simplified block diagram of the stimulation device of FIG. 1 in accordance with one embodiment of the present invention.

FIG. 2 illustrates a simplified block diagram of the stimulation device 10 in accordance with one embodiment of the present invention. The stimulation device 10 is capable of treating both fast and slow arrhythmias with stimulation therapy, including cardioversion, defibrillation, and pacing stimulation. While a particular stimulation device 10 is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40. The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode individually or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) terminal 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, the right ventricular ring electrode 34, the right ventricular coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator (Vtr. Pulse Generator) 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes a timing control circuit 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

In one embodiment, the stimulation device 10 may include an atrial sensing circuit (Atr. Sense) 82 and a ventricular sensing circuit (Vtr. Sense) 84. The atrial sensing circuit 82 and ventricular sensing circuit 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial sensing circuit 82 and ventricular sensing circuit 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, may employ one or more low power, precision amplifiers with programmable gain and/or automatic gain control, bandpass filtering, and a threshold detection circuit, as known in the art, to selectively sense the cardiac signal of interest. The bandpass filtering may include a bandpass filter that passes frequencies between 10 and 70 Hertz (Hz) and rejects frequencies below 10 Hz or above 70 Hz. The automatic gain control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart.

For arrhythmia detection, the stimulation device 10 may utilize the atrial and ventricular sensing circuits 82 and 84 to sense cardiac signals to determine whether a rhythm is physiologic or pathologic. The timing intervals between sensed events (e.g., P-waves, R-waves, and depolarization events associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar capabilities would exist on the atrial channel with respect to tachycardias occurring in the atrium. These would be atrial tachycardias (AT), more rapid atrial tachycardias (Atrial Flutter) and atrial fibrillation (AF).

In another embodiment, the stimulation device 10 may include an analog-to-digital (A/D) data acquisition circuit 90. The data acquisition circuit 90 is configured to acquire an intracardiac signal, convert the raw analog data of the intracardiac signal into a digital signal, and store the digital signals for later processing and/or telemetric transmission to an external device 102. The data acquisition circuit 90 is coupled to the right atrial lead 20, the coronary sinus lead 24, and the right ventricular lead 30 through the switch 74 to sample cardiac signals across any pair of desired electrodes. As shown in FIG. 2 the microcontroller 60 generates a control signal 92 to control operation of the data acquisition circuit 90.

The microcontroller 60 includes an arrhythmia detector 77, which operates to detect an arrhythmia, such as tachycardia and fibrillation, based on the intracardiac signal. The arrhythmia detector 77 senses R-waves in the intracardiac signal, each of which indicates a depolarization event occurring in the heart 12. The arrhythmia detector 77 may sense an R-wave by comparing a voltage amplitude of the intracardiac signal with a voltage threshold value. If the voltage amplitude of the intracardiac signal exceeds the voltage threshold value, the arrhythmia detector 77 senses the R-wave. The arrhythmia detector 77 may also determine an event time for the R-wave occurring at a peak voltage amplitude of the R-wave. The arrhythmia detector 77 may receive an analog intracardiac signal from the sensing circuits 82 and 84 or a digital intracardiac signal from the data acquisition circuit 90. Alternatively, the arrhythmia detector 77 may use the digitized intracardiac signal stored by the data acquisition circuit 90.

In one embodiment, the microcontroller 60 includes a morphology detector 99 for confirming R-waves. The morphology detector 99 compares portions of the intracardiac signal with templates of known R-waves to confirm R-waves sensed in the intracardiac signal. In various embodiments, the morphology detector 99 is optional.

The microcontroller 60 is further coupled to a memory 94 by a suitable computer bus 96 (e.g., an address and data bus), wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

In some embodiments, the stimulation device 10 further includes a physiologic sensor 108, commonly referred to as a "rate-responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. (V-V delay is typically used only in connection with independently programmable RV and LV leads for biventricular pacing.) While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 should be capable of operating at low current drains for long periods of time, and then be capable of providing high-current pulses (for capacitor charging) when the patient requires a shock pulse. The battery 110 should also have a predictable discharge characteristic so that elective replacement time can be detected. Accordingly, the stimulation device 10 may employ lithium/silver vanadium oxide batteries. As further shown in FIG. 2, the stimulation device 10 is shown as having an impedance measuring circuit 112 which is enabled by the microcontroller 60 via a control signal 114.

In the case where the stimulation device 10 is intended to operate as an implantable cardioverter/defibrillator (ICD) device, the stimulation device 10 detects and confirms the occurrence of an arrhythmia, and automatically applies an appropriate antitachycardia pacing therapy or electrical shock therapy to the heart 12 for terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and/or the SVC coil electrode 38. As noted above, the housing 40 may act as an active electrode in combination with the right ventricular coil electrode 36, or as part of a split electrical vector using the SVC coil electrode 38 or the left atrial coil electrode 28 (i.e., using the right ventricular coil electrode as a common electrode).

Cardioversion shocks are of relatively low to moderate energy level (so as to minimize the current drain on the battery) and are usually between 5 to 20 joules. Typically, cardioversion shocks are synchronized with an R-wave. Defibrillation shocks are generally of moderate to high energy level (i.e., corresponding to thresholds in the range of 15 to 40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Confirmation

The stimulation device 10 includes a confirmation unit 81, which operates to confirm that electrical events sensed in the heart 12 are depolarization events, such as R-waves and/or P-waves. The confirmation unit 81 may confirm that a sensed electrical event that has been identified as an R-wave is a depolarization event. Although discussed herein, in specific instances with respect to R-wave confirmation and ventricular events, the description also applies to P-wave confirmation and atrial events. In some embodiments, the confirmation unit 81 confirms the electrical event if a high pass filtered signal of the electrical event has an amplitude above a threshold. In some embodiments, the confirmation unit 81 confirms the electrical event if it includes sufficient power in one or more high-frequency components. In some embodiments, the confirmation unit 81 may utilize a short interval check to confirm that the electrical event is a depolarization event.

After confirmation, the arrhythmia detector 77 determines whether the confirmed electrical events (e.g., R waves) indicate an arrhythmia. In various implementations, confirmation may occur after an arrhythmia has been indicated, prior to arrhythmia detection, and/or concurrently with arrhythmia detection.

In one embodiment, the arrhythmia detector 77 senses R-waves to determine if an arrhythmia may be indicated based on the sensed R-waves. If the sensed R-waves indicate that an arrhythmia may be occurring, the confirmation unit 81 then analyzes the sensed R-waves for confirmation. The arrhythmia detector 77 then determines from the confirmed R-waves whether an arrhythmia is in fact indicated. If the confirmed R-waves indicate an arrhythmia, therapy is administered. By confirming the arrhythmia, the reliability and accuracy of the stimulation device 10 may be improved, and the inappropriate application of therapy may be reduced.

In another embodiment, the arrhythmia detector 77 confirms sensed R-waves before analyzing the sensed R-waves for an arrhythmia. For example, if a high pass filtered R-wave has an amplitude above a threshold, the confirmation unit 81 confirms that the sensed R-wave is a depolarization event. The arrhythmia detector 77 then determines whether the R-waves confirmed by the confirmation unit 81 indicate an arrhythmia. If the R-waves confirmed by the confirmation unit 81 indicate arrhythmia, therapy may be administered.

The confirmation unit 81 may use a voltage threshold to determine whether a high pass filtered signal has sufficient peak voltage amplitude. By using a voltage threshold, high-frequency noise signals having peak voltage amplitudes below the voltage threshold are not considered high-frequency components of the R-wave. The voltage threshold may be a fixed voltage value, or it may be a declining voltage value, one that decreases over time.

In one embodiment, the voltage threshold is determined based on the maximum voltage amplitude of the last sensed R-wave, and has a declining value. In one example implementation, the voltage threshold may be mathematically represented as follows.

$$TDect = \max(\max(\min(T_{LastR}, MaxFiltR), MinFiltR) * ThrStart - DecayRate * (t_R - t_{LastR})), MaxSensitivity), \text{ where:}$$

TDect is the voltage threshold $T_{LastR}$ is a peak voltage amplitude of the last R-wave MaxFiltR is a maximum voltage amplitude for the last R-wave MinFiltR is a minimum voltage amplitude for the last R-wave ThrStart is a factor for reducing the start voltage of the threshold DecayRate is a declining rate of the voltage threshold over time $t_R$ is the event time of the R-wave $t_{LastR}$ is the event time of the last R-wave MaxSensitivity is a minimum voltage threshold For example, MaxFiltR may be set to 3 mV, MinFiltR may be 0.5 mV, ThrStart may be set to 0.5, DecayRate may be set to 3 mV/s, and MaxSensitivity may be set to 0.2 mV.

In one particular embodiment, the confirmation unit 81 generates a filtered signal by high pass filtering sensed R-waves of an intracardiac signal with a high pass filter having a cutoff frequency in a range of about 15 Hz to about 40 Hz. For example, in one implementation, the high pass filter has a cutoff frequency of about 20 Hz. In another implementation, the high pass filter has a cutoff frequency of about 30 Hz. In yet another implementation, the high pass filter has a cutoff frequency of about 35 Hz. In still another implementation, the high pass filter has a cutoff frequency of about 40 Hz. The confirmation unit 81 determines whether the sensed R-wave is a depolarization event by comparing the amplitude of the filtered R-wave at the event time of the sensed R-wave with a voltage threshold. If the amplitude of the filtered signal at the event time of the sensed R-wave exceeds the voltage threshold, the confirmation unit 81 confirms the sensed R-wave.

R-wave confirmation could be carried out in the frequency domain, as well as in the time domain. Thus, in an alternate implementation, it is possible to use frequency domain analysis to determine whether the R-wave includes a high-frequency component. In one embodiment, the confirmation unit 81 analyzes the frequency components of the R-wave and determines whether the R-wave includes one or more selected high-frequency component(s), at or above a selected frequency. For example, the frequency spectrum may indicate the power, or voltage amplitude, of one or more selected frequency components in the R-wave. If the frequency spectrum includes one or more selected high-frequency components above a threshold value, the confirmation unit 81 confirms the R-wave.

The confirmation unit 81 may operate to confirm R-waves from real time sensed electrical activity, or from a stored version of the sensed electrical activity, such as electrogram or EGM data. Confirmation from stored EGM data facilitates a window analysis of the EGM data around identified and/or suspected R-waves. The confirmation unit 81 may determine whether an electrical event includes a high-frequency component by determining whether a portion of the electrogram signal within a time window around the event time of the electrical event includes the high-frequency component. The confirmation unit 81 may high pass filter the stored version of the sensed electrical activity and determine whether the high pass filtered version of the sensed electrical activity is above a threshold voltage.

As such, in certain embodiments, a time window with an interval in a range of about 80 to 100 milliseconds may be used. For example, the time window may start around the time of the electrical event and end 80 to 100 milliseconds after the event time. The confirmation unit 81 may access a portion of the intracardiac signal within the time window from the digitized intracardiac signal stored by the data acquisition circuit 90. In this way, the confirmation unit 81 can confirm electrical events by analyzing those portions of the intracardiac signal within time windows, which may reduce power consumption in the stimulation device 10.

In some embodiments, a time window with an interval range of about 15 to 30 milliseconds may be used. For example, the window may start around about 10 to 0 milliseconds prior to the electrical event and end 15 to 25 milliseconds after the electrical event. The confirmation unit 81 may access a portion of the intracardiac signal within the time window from the digitized intracardiac signal stored by the data acquisition circuit 90. In this way, the confirmation unit 81 can confirm the electrical event by analyzing only a short portion of the intracardiac signal within time windows, which may reduce power consumption in the stimulation device 10, and may allow cardioversion therapy and antitachycardia pacing to be delivered into ventricular signals that are confirmed to be depolarization events.

In certain embodiments, a short interval check may be used to confirm that an electrical event is a depolarization event. During fibrillation, the ventricular depolarization events often due not have as high of frequency components. In such embodiments, the timing control circuit 79 may track a refractory period and a short interval following an event time of an electrical event (e.g., an R-wave). The refractory period is the minimum time for sensing a subsequent electrical event. The confirmation unit 81 analyzes the sensed signal, such as the intracardiac signal, within the short interval to determine if an electrical event has been sensed within the short interval. If an electrical event is sensed/detected within the short interval it is confirmed as a depolarization event.

The arrhythmia detector 77 does not analyze the intracardiac signal for a subsequent R-wave in the refractory period because such an R-wave should not occur in the refractory period. For example, a refractory period may last for 185 milliseconds, and two R-waves separated by 185 milliseconds indicate a heart rate of 324 beats per minute. Such a high heart rate does not typically occur in tachycardia or fibrillation.

At the onset of fibrillation, however, multiple sites in the heart are depolarizing asynchronously, creating more rapid pattern of ventricular sensed signals than in normal heart beats. This lack of synchronization can lead to lower frequency components in the depolarization event. This can lead to rapid sensing in the ventricular channel, with short intervals occurring following the refractory period of a first sensed signal to the subsequent sensed signal. For example, the short interval may have a duration of less than 50 ms following the end of the previous sensed signal's refractory period. Two sensed signals R-waves separated by 220 milliseconds in total time, or about 25 to 50 ms following the end of the previous sensed signal's refractory period indicate a heart rate of 272 beats per minute, which may be fibrillation. The short interval should end before a subsequent T-wave following the R-wave so that the T-wave is not incorrectly sensed as a subsequent R-wave. The repolarization does not typically start in the patient population for ICDs until at least 240 ms after the start of the depolarization event. This can provide an upper limit of 240 ms from the start of the sensing of the depolarization event to the end of the short check window. Because the voltage amplitude and frequency components of an R-wave during fibrillation may be lower than those of the previous R-wave, the confirmation unit 81 confirms the R-wave in the short interval without determining whether this R-wave includes a high-frequency component. By confirming an R-wave occurring in the short interval regardless of a high-frequency component in the R-wave, the sensitivity of the arrhythmia detector 77 for detecting fibrillation is increased so that therapy may be appropriately applied to the heart 12.

Although the confirmation unit 81 is shown as part of the microcontroller 60 in FIG. 2, the confirmation unit 81 or portions thereof may be outside the microcontroller 60. In various embodiments, the confirmation unit 81 may include a hardware module coupled in communication with the microcontroller 60 or a software module in the memory 94. For example, a hardware module may be a finite state machine or a digital signal processor, and the software module may be processor executable instructions. The instructions may be contained in a processor readable medium accessible by the microcontroller 60. For example, the microcontroller 60 may include firmware containing the instructions, or the memory 94 may store the instructions.

Although shown as being components of the microcontroller 60, any or all of the arrhythmia detector 77, the timing control circuit 79, the confirmation unit 81, or the optional morphology detector 99 may be instead implemented as separate components. Also, depending upon the particular component and the particular implementation, individual components may be configured to apply to the ventricles, the atria, or in some cases both.

In one embodiment, the confirmation unit 81 includes executable instructions, which the microcontroller 60 executes to determine whether an R-wave includes one or more high-frequency components. If the filtered R-wave has a sufficient peak amplitude, the confirmation unit 81 confirms the R-wave. The instructions may include instructions for high pass filtering the R-wave to generate a filtered signal. For example, the instructions may include instructions for implementing a filter that passes frequencies above 30 Hz and suppresses frequencies below 30 Hz. For example, the filter may be a 6 pole Kaiser window finite impulse response high pass filter having a cutoff frequency of 30 Hz and a β of 1.2. As a second example of the filter, the 6 pole Kaiser window finite impulse response high pass filter may be adapted, shortening the filter by 2 points from the front side and 1 point on the back side to allow for more rapid pass processing and lowering the group delay of the filter which can postpone confirmation. As a third example, an analog type filter such as an Chebyshev Type II filter with 3 poles and zeros, zeros at (0.9493+0.3143i radians), (0.9493−0.3143i radians) and poles at (0.6148 radians, 0.7172+0.3846i radians, and 0.7172−0.3846i radians) could be used. Other pole and zero combinations providing similar filtering characteristics with respect to a stop band and a pass band could be used as alternatives. The instructions may also include instructions for comparing the voltage amplitude of the filtered signal at the event time of the R-wave with a voltage to determine whether the R-wave includes a high-frequency component. Alternatively, the instructions may include instructions for generating a frequency spectrum of the R-wave and determining whether the frequency spectrum includes a high-frequency component.

Figure 3:
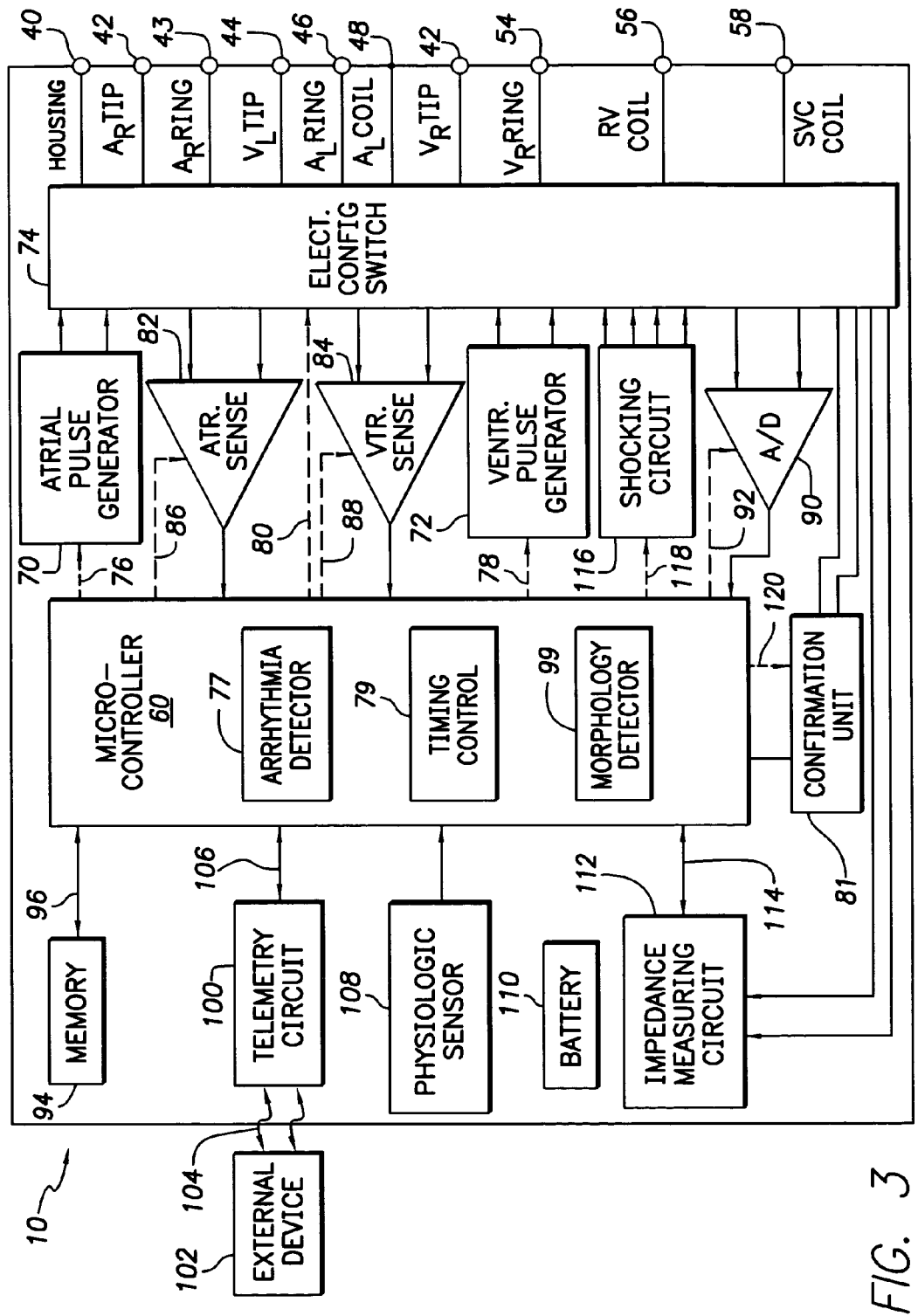
FIG. 3 is a simplified block diagram of the stimulation device of FIG. 1 in accordance with another embodiment of the present invention.

FIG. 3 illustrates a simplified block diagram of the stimulation device 10 in accordance with one embodiment of the present invention. The stimulation device of FIG. 3 is similar to the stimulation device of FIG. 2, but the confirmation unit 81 is located outside the microcontroller 60. The confirmation unit 81 acquires an intracardiac signal, performs a high pass filter of the intracardiac signal to generate a filtered signal. The filtered signal is analyzed for a high-frequency component at or near the (The window of time either 80 ms or 25 ms is typically after the sensed event) event time of an R-wave. If the filtered signal includes a high-frequency component at the event time of the R-wave, the R-wave is confirmed either by the confirmation unit 81, or by the microcontroller 60. For example, the confirmation unit 81 may confirm the R-wave by sending a signal to the microcontroller 60 indicating that the R-wave includes a high-frequency component.

Although the confirmation unit 81 is shown coupled directly to the switch 74, in other embodiments it may be coupled via the sense circuits 82 and/or 84, the data acquisition circuit 90, memory 94, or other circuitry. Furthermore, although shown coupled direction to the microcontroller 60, in some embodiments, the confirmation unit 81 may be coupled through an A/D converter (not shown), a detection circuit (not shown), or other circuit. As shown in FIG. 3 the microcontroller 60 may be coupled to the confirmation unit 81, and may supply control and/or data signals 120 to the confirmation unit 81. For example, control signals may indicate an event time of a sensed R-wave, or provide parameters (e.g., a voltage or frequency threshold) for analyzing the intracardiac signal or data.

Figure 4:
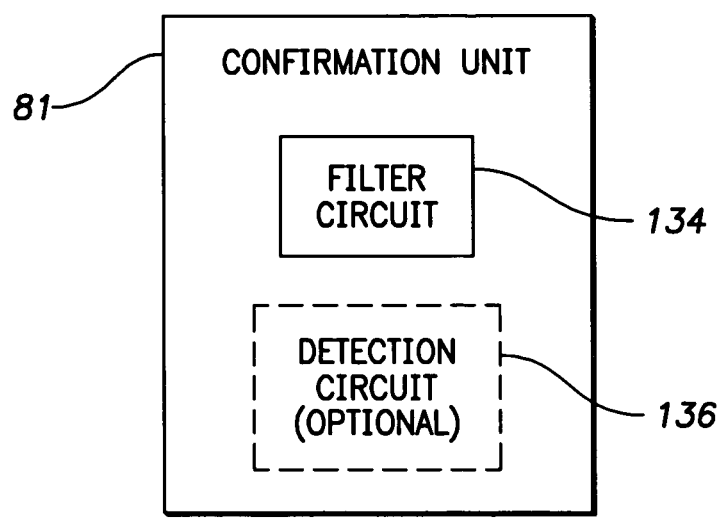
FIG. 4 is a functional block diagram of one embodiment of an R-wave confirmation unit in accordance with one embodiment of the present invention.

FIG. 4 illustrates an embodiment of the confirmation unit 81 shown in FIG. 3. The confirmation unit 81 includes a filter circuit 134 that performs a high pass filtering operation on the R-wave to generate a filtered signal. For example, the filter circuit 134 may include a 6 pole high pass sampling filter having an ω of 0.1172 radians and a sampling rate of 128 Hz. The filter circuit 134 may generate a digital filtered signal and provide the digital filtered signal to the microcontroller 60. In turn, the microcontroller 60 determines whether the digital filtered signal has a sufficient peak amplitude.

In another embodiment, the confirmation unit 81 includes an optional detection circuit 136. The filter circuit 134 generates the filtered signal, and the detection circuit 136 determines whether the filtered signal has a sufficient peak amplitude. The detection circuit 136 may include a voltage comparator that compares the voltage amplitude of the filtered signal with a voltage. Alternatively, the filter circuit 134 may generate an analog filtered signal and the detection circuit 136 can convert the analog filtered signal into a digital filtered signal. In this way, the detection circuit 136 detects the amplitude of the filtered signal. In turn, the microcontroller 60 determines whether the digital filtered signal has a sufficient peak amplitude.

In one embodiment, the confirmation unit 81 can confirm one or more R-waves in a sequence of R-waves substantially simultaneously with the arrhythmia detector 77 sensing the sequence of R-waves. For example, the confirmation unit 81 may confirm an R-wave within 25 ms of sensing the R-wave. In this way, the arrhythmia detector 77 may decrease the time for confirming a detected arrhythmia.

In another embodiment, the confirmation unit 81 may perform confirmation after an arrhythmia has been identified, but before therapy is delivered. For example, R-wave confirmation may be performed while the shocking circuit 116 is preparing to deliver therapy, i.e., while the shocking circuit is charging.

Figure 5:
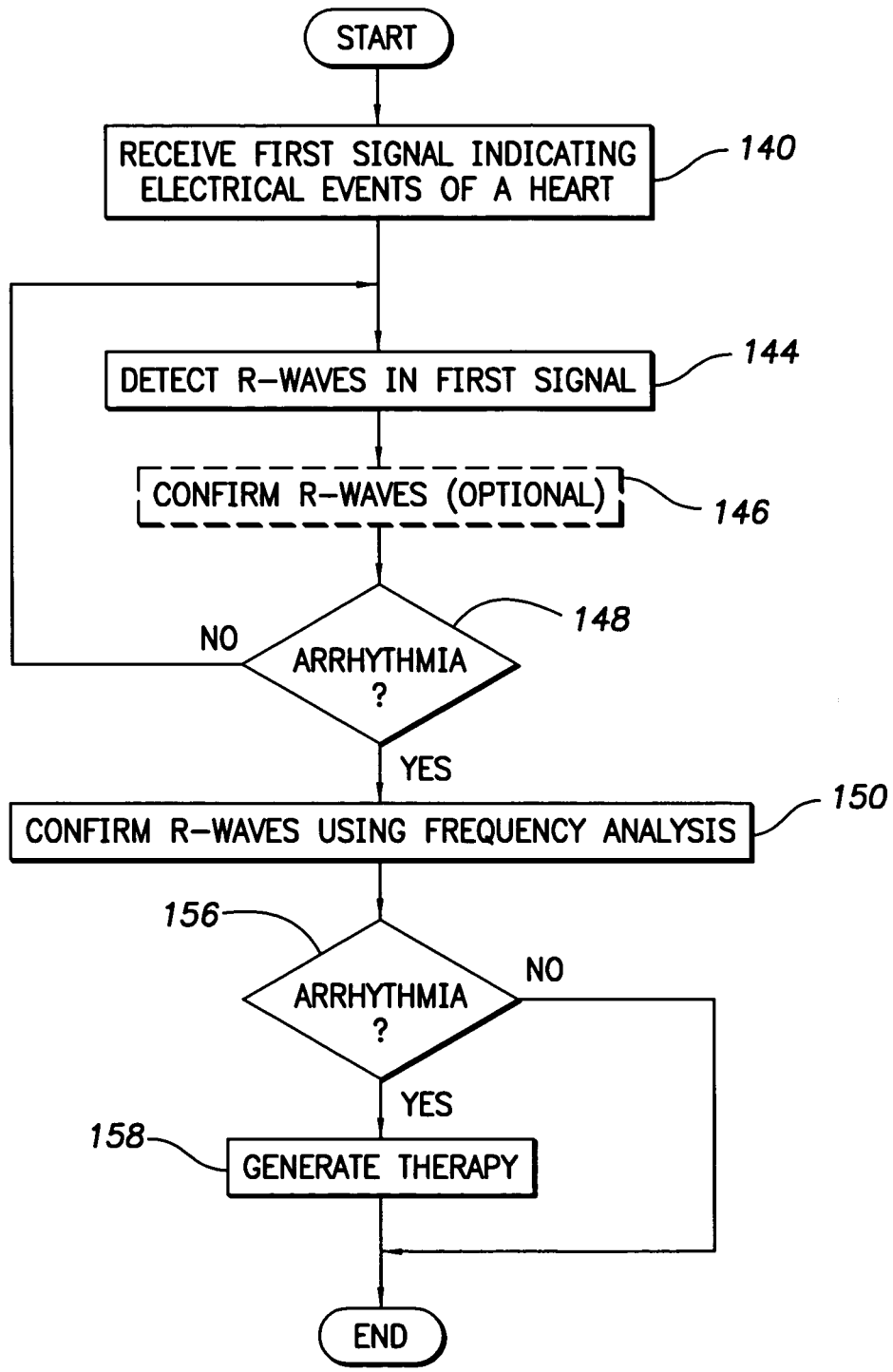
FIG. 5 is a flow chart illustrating a method of treating an arrhythmia in accordance with one embodiment of the present invention.
Figure 6:
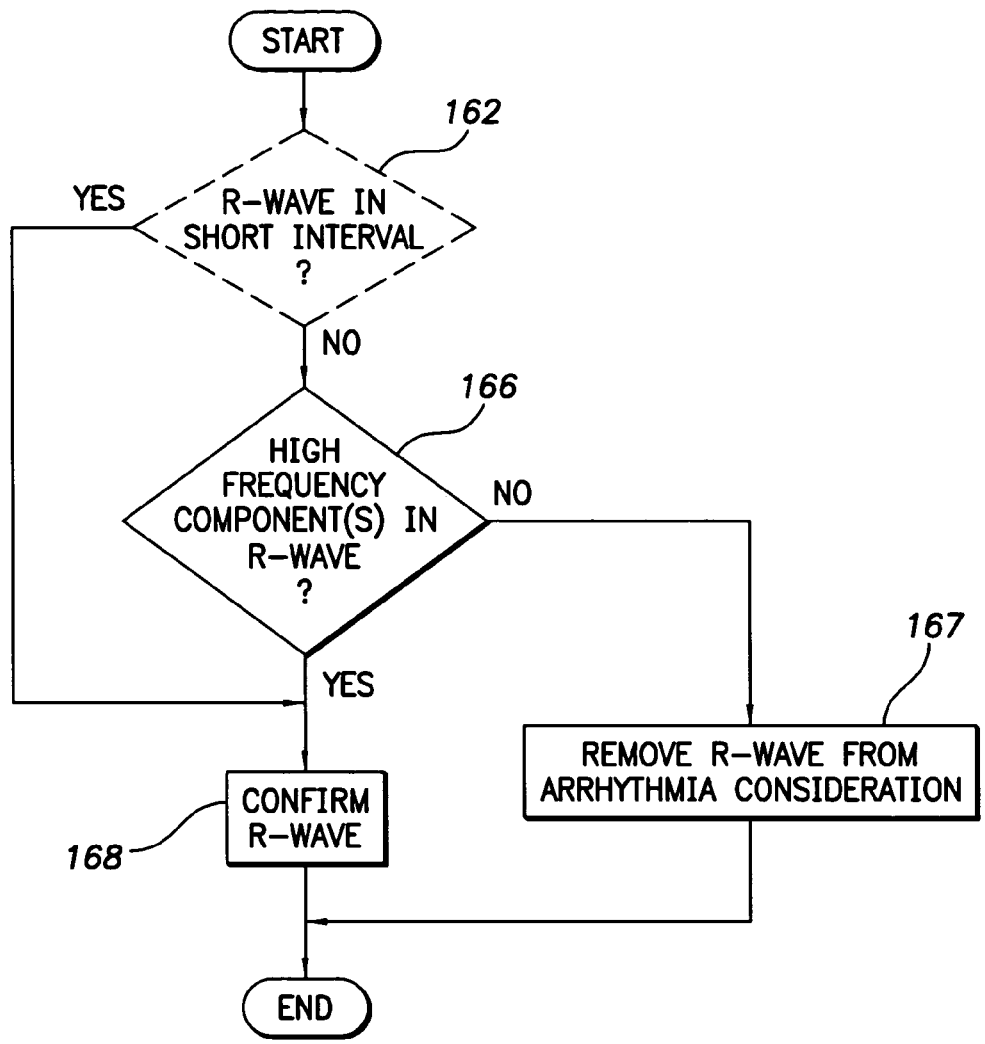
FIG. 6 is a flow chart illustrating a portion of the method of FIG. 5 for confirming an R-wave in accordance with one embodiment of the present invention.
Figure 7:
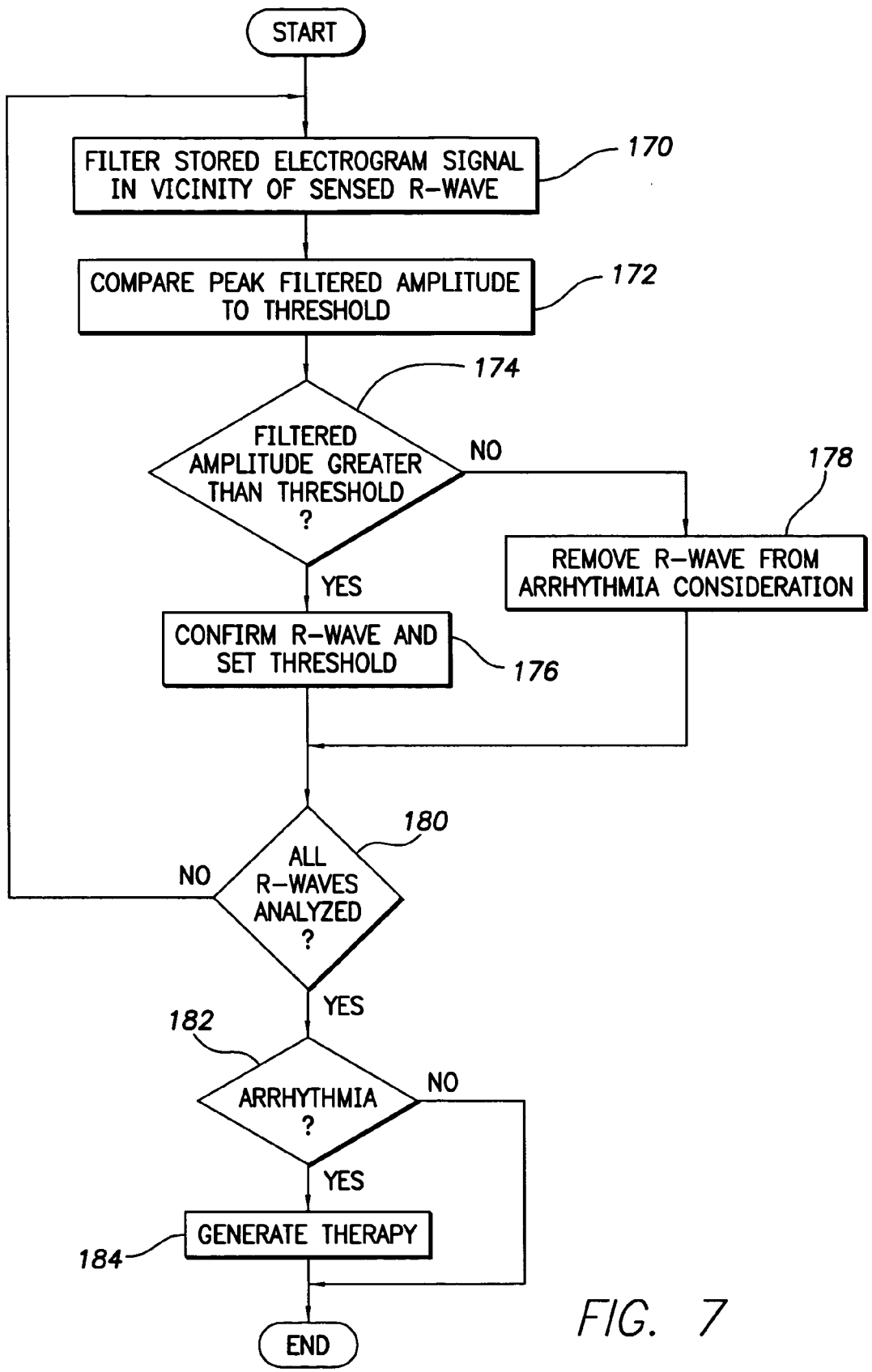
FIG. 7 is a flow chart illustrating the method of treating an arrhythmia in accordance with another embodiment of the present invention.

Referring to the FIGS. 5-7, flow charts are shown illustrating certain potential implementations of methods in accordance with the present invention. Other implementations are possible.

FIG. 5 illustrates a flow chart of a method for an implantable stimulation device 10 in accordance with one embodiment of the present invention. In step 140, the stimulation device 10 receives a first signal indicating electrical events of the heart 12, such as depolarization events and repolarization events. For example, the first signal may represent a natural sinus rhythm of the heart or an arrhythmia such as tachycardia or fibrillation. The first signal may be an electrical signal, such as an intracardiac signal, which is transmitted from the heart 12 to the simulation device 10 via the leads 20, 24, and 30 shown in FIG. 1. The sensing circuits 82 and 84 or the data acquisition circuit 90 may process the intracardiac signal to generate the first signal. For example, the sensing circuits 82 and 84 may amplify and filter the intracardiac signal, or the data acquisition circuit 90 may digitize the intracardiac signal.

The R-waves in the first signal are detected 144, and the arrhythmia detector 77 determines if an arrhythmia is occurring 148. In step 148, the arrhythmia detector 77 determines whether a sequence of R-waves, along with other indicators, indicates an arrhythmia occurring in the heart 12. In an optional step 146, the R-waves may be confirmed prior to determining whether an arrhythmia exists. Typically, if the voltage amplitude of the first signal exceeds the voltage threshold, the arrhythmia detector 77 senses the R-wave. The voltage threshold may be a voltage threshold that declines in amplitude after the R-wave. In this way, the sensitivity of the arrhythmia detector 77 for sensing R-waves progressively increases after the R-wave. The arrhythmia detector 77 also establishes an event time (not illustrated) for the R-wave by, for example, determining a peak voltage amplitude of the R-wave.

If an arrhythmia is detected at 148, the R-waves are confirmed, for example, with the short interval method by examining the high-frequency component of the R-wave. The confirmation unit 81 may confirm all, some, or none of the R-waves in the sequence of R-waves. In one embodiment, the confirmation unit 81 confirms all R-waves within a short interval following the R-wave as is described more fully herein. In other implementations filtering and/or high-frequency analysis is performed to confirm R-waves.

In step 156, the arrhythmia detector 77 determines whether the R-waves confirmed by the confirmation unit 81 indicate the arrhythmia detected in step 148. The arrhythmia detector 77 may use the same methods of step 148 to determine whether the confirmed R-waves indicate the detected arrhythmia but with confirmed R-waves.

It should be noted that if R-wave confirmation is used in step 146, R-wave confirmation in step 150 is optional and not required. Similarly, if R-wave confirmation is performed in step 146, arrhythmia detection in step 156 may be omitted.

If the confirmed R-waves indicate arrhythmia, the arrhythmia detector 77 confirms the detected arrhythmia and therapy is provided at step 158. Otherwise, if the arrhythmia detector 77 determines that the confirmed R-waves do not indicate the detected arrhythmia, therapy is not generated. The method may operate in a continuous manner to determine whether subsequent R-waves indicate an arrhythmia.

In step 158, the stimulation device 10 generates a therapy in response to the confirmation of the arrhythmia in step 156.

For example, the stimulation device 10 may generate a shocking therapy to treat the heart 12.

FIG. 6 illustrates a flow chart for an implementation for confirming an R-wave. In step 162, a short interval check is performed to determine whether the R-wave is within the short interval. If the R-wave is in the short interval, the R-wave is confirmed at 168. Otherwise, a high-frequency check is performed at 166. If the high-frequency check indicates there is sufficient amplitude of the high pass filtered signal, or that frequency analysis indicates that sufficient amplitude of high frequency components exist in the R-wave, the R-wave is confirmed at 168. If this is not the case, the R-wave is removed from consideration at 167. In various embodiments, step 162 is optional.

In one implementation, the confirmation unit 81 determines in step 166 whether the R-wave includes one or more high-frequency components. In one embodiment, the confirmation unit 81 determines whether the R-wave includes a high-frequency component by comparing the peak voltage amplitude of the high pass filtered R-wave with a voltage threshold. In another embodiment, the confirmation unit 81 generates a frequency spectrum of the R-wave and determines whether the frequency spectrum includes a high-frequency component having a frequency above the selected frequency. If the confirmation unit 81 determines that the R-wave includes one or more high-frequency components, the R-wave may be confirmed at 168 on this basis.

In one implementation, the confirmation unit 81 performs a high pass filtering operation on the first signal to generate a second signal. For example, the R-wave confirmation may include high pass filtering of the first signal by using a high pass finite impulse response filter implemented in processor executable instructions or by using a high pass digital sampling filter. The confirmation unit 81 may perform high pass filtering of the first signal within a time window around the event time of the R-wave. For example, the data acquisition circuit 90 can digitize the first signal and store the digitized first signal into the memory 94, and the confirmation unit 81 may access a portion of the digitized first signal within the time window from the memory 94. By high pass filtering the first signal within the time window instead of continuously high pass filtering the first signal, the confirmation unit 81 may use less power to generate the second signal and the power consumption of the stimulation device 10 may be reduced. Further, by confirming R-waves only after an arrhythmia has been detected, power consumption can be reduced.

FIG. 7 illustrates a flow chart of a method for an implantable device in accordance with some embodiments of the present invention. In step 170, a stored intracardiac signal is filtered in the vicinity of the sensed R-wave, i.e., within a window about the R-wave. The stored intracardiac signal may be an electrogram retrieved from the memory 94, for example.

The peak filtered amplitude is compared to a threshold at 172. If the peak filtered amplitude is greater than the voltage threshold amplitude at 174, the R-wave is confirmed at 176. The confirmation unit 81 may set a voltage threshold to a fraction of the peak filtered amplitude and may establish a declining threshold as is described more fully herein. If the peak filtered amplitude is not greater than a threshold, the R-wave is removed from consideration 179.

After all R-waves of interest have been analyzed, it is determined whether arrhythmia exists at 182, and an appropriate therapy is generated at 184 if arrhythmia exists. In this way, the method operates in a continuous, or on an as needed basis, to confirm R-waves.

Thus, some implementations and embodiments can reduce T-wave oversensing by removing from arrhythmia detection, T-waves incorrectly identified as R-waves. Moreover, some implementations and embodiments can provide a low power means to confirm R-waves for use in arrhythmia detection. As such, some implementations and embodiments improve fibrillation detection when T-wave oversensing is a particular concern.

As can be appreciated a wide variety of techniques can be implemented consistent with the principles the invention and no attempt is made herein to describe all possible capture-based tachycardia detection techniques, DAO/ATP switching techniques, DAO/ATP set up techniques, backup pulse capture detection techniques or ventricular fibrillation detection techniques. Although described primarily with reference to an example wherein the implanted device is a defibrillation/pacer, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method capable of use in an implantable cardiac stimulation device, the method comprising:
    detecting a plurality of cardiac events;
    identifying a potential arrhythmia from the plurality of cardiac events;
    confirming a first one of the plurality of cardiac event is an R-wave if it is detected within a short interval after a refractory period following a previous R-wave;
    high pass filtering the first one of the plurality of cardiac events to confirm it is an R-wave if the short interval check does not confirm that the cardiac event is an R-wave; and
    determining whether to deliver therapy based on the confirmation of the cardiac events.

2. The method of claim 1, wherein performing the confirmation comprises performing a short interval check on an R-wave within a time window of about 25 milliseconds after a refractory period following a previous R-wave.

3. The method of claim 1, wherein performing the R-wave confirmation comprises performing a short interval check on an R-wave within a time window of about 185 milliseconds to about 210 milliseconds after a previous R-wave.

4. The method of claim 1, further comprising storing an intracardiac signal into a memory, wherein performing the confirmation comprises performing a confirmation of the stored intracardiac signal.

5. The method of claim 4, wherein performing the confirmation of the stored intracardiac signal comprises:
    selecting a time window corresponding to an R-wave from the stored intracardiac signal; and
    performing a confirmation on the stored intracardiac signal within the selected time window of the R wave.

6. The method of claim 5, wherein the time window comprises a duration in a range from about 80 milliseconds to about 100 milliseconds.

7. The method of claim 5, wherein the time window comprises a duration in a range from about 15 milliseconds to about 25 milliseconds.

8. The method of claim 1, further comprising at least one of: a) performing the confirmation after identifying the potential arrhythmia; b) performing the confirmation before identifying the potential arrhythmia; or c) performing the confirmation along with identifying the potential arrhythmia.

\* \* \* \* \*